United States Patent [19]

Yamada et al.

[11] Patent Number: 5,196,583
[45] Date of Patent: Mar. 23, 1993

[54] PROPARGYL AMINO COMPOUNDS

[75] Inventors: Mitsuo Yamada, Osaka; Kei Aoki, Nara, both of Japan

[73] Assignee: Nippon Paint Co., Ltd., Osaka, Japan

[21] Appl. No.: 621,440

[22] Filed: Dec. 4, 1990

[30] Foreign Application Priority Data

Dec. 4, 1989 [JP] Japan .................................. 1-315852

[51] Int. Cl.$^5$ .......................................... C07C 211/22
[52] U.S. Cl. ..................... 564/305; 544/382; 558/418; 558/428; 558/431; 558/432; 558/437; 558/452; 564/307; 564/308; 564/309; 564/315; 564/330; 564/428; 564/430; 564/441; 564/442; 564/443; 564/461; 564/503; 564/509
[58] Field of Search ............... 564/305, 307, 308, 309, 564/315, 330, 430, 441, 442, 443, 428, 461, 503, 509; 544/382; 558/418, 428, 431, 432, 437, 452

[56] References Cited

U.S. PATENT DOCUMENTS

| | | | |
|---|---|---|---|
| 3,121,116 | 2/1964 | Pawloski | 564/305 |
| 3,121,745 | 2/1964 | Pawloski | 564/441 |
| 3,149,160 | 9/1964 | Pawloski | 564/442 |
| 3,268,524 | 8/1966 | Moore et al. | 564/305 |
| 3,299,141 | 1/1967 | Croxall | 564/305 |
| 4,301,158 | 11/1981 | Spencer | 564/441 |
| 4,431,671 | 2/1984 | Ehrenfreund | 564/305 |
| 4,699,910 | 10/1987 | Banholzer et al. | 564/305 |

FOREIGN PATENT DOCUMENTS 2528345 1/1976 Fed. Rep. of Germany ...... 564/430

OTHER PUBLICATIONS

Sladkov et al, Chemical Abstracts, vol. 68 (1968) 95413c.
Shabanova et al, Chemical Abstracts, vol. 69 (1968) 77834g.
Shabanova et al, Chemical Abstracts, vol. 70 (1969) 28220r.

Primary Examiner—Richard L. Raymond
Attorney, Agent, or Firm—Wenderoth, Lind & Ponack

[57] ABSTRACT

The invention provides a novel class of propargyl compounds represented by the formula:

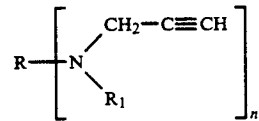

wherein R is an $C_1$-$C_{20}$ alkyl group, $C_1$-$C_{20}$ alkylene group, $C_1$-$C_{20}$ alkylene group interrupted by —NH— group(s), $C_6$-$C_7$ alicyclic group and an aromatic group; $R_1$ comprises 1-100% —$CH_2$—C≡CH group and 99-0% hydrogen atom and n is an integer of 1 to 4, and preparation thereof.

These compounds are useful as coating material or sealer or rim-injection molding material.

7 Claims, No Drawings

PROPARGYL AMINO COMPOUNDS

FIELD OF INVENTION

The present invention relates to a novel class of propargyl compounds and preparation thereof.

The invention also concerns a coating composition, a sealer and a molding material containing the same.

BACKGROUND OF THE INVENTION

Recently, various resins are used for the coating of electric or electronic parts, automobile and airplane parts, plant parts and the like.

In curing such resinous material, methods for using a curing agent as aminoplast resin or isocyanate compound (including blocked isocyanate compound) or effecting oxidative polymerization of resinous material itself have been widely used.

However, in the curing method with an aminoplast resin, there are such problems as liberation of the formed alcohol or water and thermal instability of the formed bond, and in the curing method with an isocyanate compound, a difficult problem of workability.

Further more, in the curing method of relying on an oxidative polymerization of resinous material, it is essential to adopt an elevated temperature which is not economical and undesired.

Under the circumstances, a novel curing system has been longed for.

A compound having an acetylenic group or propargyl group can exhibit various reactivities as diene polymerization reactivity, oxidative coupling property, trimerization or tetramerization property and the like.

Such reactions can be easily proceeded with by the application of photo-, thermal or electric energy.

Especially, such compound can give a high molecular weight compound through polycondensation reaction by the application of thermal energy, and since the reaction does not accompany with the formation of any volatile material or liberated product, public attention is directed to this novel curing system.

Many compounds having end acetylenic or propargyl groups have been reported in various publications (unexamined) 55-94351, ibid 55-94352 and ibid 63-117034.

Regarding propargyl compounds, U.S. Pat. No. 3,386,897 discloses

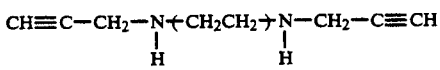

and U.S. patent application No. 199768, discloses compounds of the formula:

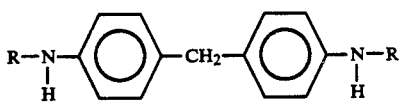

in which 1-100% of R stands for —$CH_2$—C≡CH and 99-0% of R, $CH_3$.

However, all of the heretofore proposed propargyl compounds are mono-substituted amine compounds which have rather poor reactivities of propargyl group.

It is, therefore, an object of the invention to provide a novel class of propargyl Compounds which have improved reactivities and are useful as coating material or sealer for aircraft parts, plant material, electric or electronic parts and the like or as rim-injection-molding material.

DETAILS OF THE INVENTION

According to the invention, the abovementioned object can be attained with a class of propargyl compounds represented by the formula:

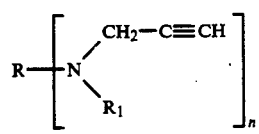

wherein R is an alkyl group having 1 to 20 carbon atoms, an alkylene group having 1 to 20 carbon atoms, an alkylene group having 2 to 20 carbon atoms interrupted by —NH— group(s), an alicyclic group having 6 to 7 carbon atoms, and aromatic group selected from benzene, naphthalene, biphenyl, diphenyl methane, diphenyl sulfone and the like, a piperazine or spiro undecane, optionally substituted by lower alkyl, halogen, nitro, lower alkoxy or cyano group; $R_1$ stands for 1-100% —$CH_2$—C≡CH group and 99-0% H; and n is an integer of 1 to 4.

They are all novel compounds and may be advantageously prepared by the reaction of 1 mol of amine compound represented by the formula:

in which R and n are as defined above, and 1.05-6 mols of propargyl halide.

The objective propargyl compound is, therefore provided in the from of compound [III]: compound [IV]=100:0-1:99.

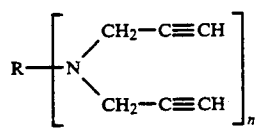

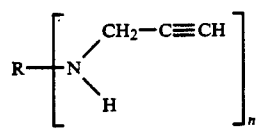

and is characterized by always including 1% or more of the compound [III].

The present propargyl compound may be used as coating material or sealer in the form of said mixture.

However, if desired, the abovementioned compound [III] is separated and purified and then used in the same way.

In the actual production of such propargyl compound [III], 1 mol of the amine compound [II]

and 2-6 mols of propargyl halide are reacted, preferably in water-organic solvent system, in the presence of an phase transfer catalyst the reaction product obtained is subjected to a column chromatography to obtain a pure compound [III].

As the starting amine compounds [II], many compounds are available in the market and the following may be satisfactorily used.

Monoamines: ethylamine, butylamine, propylamine, aniline, methylaniline and the like.

Polyamines:

Aliphatics: ethylene diamine, 1,2-diamino propane, 1,3-diamino propane, 1,2-diamino butane, 1,3-diamino butane, 1,4-diamino butane, 1,5-diamino pentane, 1,6-hexane diamine, 1,9-diamino nonane, 1,10-diamino decane, 1,12-diamino dodecane, polymethylene diamines having up to 20 carbon atoms, and the like.

Alicyclics: N-aminoethyl piperazine, Ramiron C-260 (BASF), isophoron diamine (Huls), wondamine HM (Shin Nihon Rika), 1,3-BAC (Mitsubishi Gas Chem. Co.), diamino cyclohexane and the like.

Aromatics: diamine compounds represented by the formula:

H$_2$N—R—NH$_2$ (R is a bivalent organic group) as, for example, 4,4'-bis (4-aminophenoxy) biphenyl, 4,4'-diamino diphenyl sulfone, 3,3'-diamino diphenyl sulfone, bis [4-(4-aminophenoxy) phenyl] sulfone, bis [4-(3-aminophenoxy) phenyl] sulfone, bis [4-(2-aminophenoxy) phenyl] sulfone, 1,4-bis (4-aminophenoxy) benzene, 1,3-bis (4aminophenoxy benzene, 1,3-bis (3-aminophenoxy) benzene, 1,4-bis (4-aminophenyl) benzene, bis[4-(4-aminophenoxy) phenyl] ether, bis(3-ethyl-4aminophenyl) methane, bis (3-chloro-4-aminophenyl) methane, 3,3'-diamino phenyl sulfone, 4,4'-diamino phenyl sulfone, 4,4'-diamino phenyl sulfide, 3,3'-diamino diphenyl ether, 3,4'-diamino phenyl ether, 4,4'-diamino phenyl ether, 4,4'-diamino phenyl methane, 2,4'-diamino toluene, methaphenylene diamine, 2,2'-bis [4-(4-aminophenoxy) phenyl] propane, 2,2'-bis [4-(4-aminophenoxy) phenyl] hexafluoropropane, 2,2'-bis (4-aminophenyl) propane, 2,2'-bis (4-aminophenyl) hexafluoropropane, 2,2'-bis (3-hydroxy-4-aminophenyl) propane, 2,2'-bis (3-hydroxy-4-aminophenyl) hexafluoropropane, 9,9'-bis (4-aminophenyl)-10-hydro-anthracene, ortho tolidine sulfon, 3,3',4,4'-biphenyl tetramine, 3,3',4,4'-tetraamino diphenyl ether and other polyamines, 4,4'-diamino-2,3,5,6,2',3',5',6'-octafluorobiphenyl, 3,9-bis (3-aminopropyl) 2,4,8,10-tetraspiro (5,5) undecane and the like.

Examples of propargyl halide are propargyl bromide, propalgyl chloride and the like.

These compounds (amine and propargyl halide) are reacted each other at an elevated temperature, preferably in a mixed medium of water and organic solvent and in the presence of phase transfer catalyst comprising delydrohalogenation agent and quaternary ammonium salt (e.g. NaOH-tetra-ammonium bromide).

As already stated, the present propargyl compound does always include the di-substituted compound of the formula [III], and therefore, 1.1 mol or more, preferably 2 to 6 mols of propargyl halide should be reacted with 1 mol of amine compound [II].

If desired, the reaction product thus obtained is subjected to silica gel column chromatography to separate the di-substituted compound [III], which is then purified by means of recrystallization with an appropriate solvent.

Thus obtained propargyl compound of the present invention is characterized by having far improved reactivities of the propargyl group contained, as compared with that of monosubstituted derivative, including co-reaction activities toward olefinic compound.

Thus, the present propargyl compound is excellent in diene polymerization reactivity, oxidative coupling reactivity, trimerization or tetramerization reactivity and such reactions may be easily carried out by the application of photo-, thermal or electric energy.

Therefore, the present propargyl compounds are quite useful, by themselves or in the combination with other high molecular weight binder materials, as coating material or sealer for various substrates.

In the mixture of compound [III] and [IV], there always exist 1% or more compound [IV], and hence, initiation of trimerization or tetramerization reaction is greatly enhanced.

The present invention shall be now more fully explained in the following Examples.

EXAMPLE 1

Into a reaction vessel fitted with a stirrer, a reflux condenser and a nitrogen gas inlet tube, were placed 30.05 g (0.5 mol) of ethylene diamine, 84.21 g of sodium hydroxide, 180 g of deionized water.

180 g of methylene chloride and 1.0 g of tetrabutylammonium bromide and the mixture was stirred and added dropwise with 249.81 g (2.1 mols) of propargyl bromide at a room temperature.

After completion of said addition, the mixture was heated to 50° C. and reacted at the same temperature for 6 hours.

Therefore, using a separate funnel, methylene chloride layer was separated from an aqueous layer, washed with deionized water several times and then the solvent was removed off to obtain a crude product.

The product was subjected to silica gel column chromatography (Wako Gel C-200) to obtain purified N,N,N',N'-tetra propargyl ethylene diamine (yield 92%).

EXAMPLE 2

Into a reaction vessel fitted with a stirrer, a reflux condenser and a nitrogen gas inlet tube, were placed 99.12 g (0.5 mol) of p,p'-diamino diphenyl methane, 84.21 g of sodium hydroxide, 180 g of deionized water, 180 g of dichloroethane and 1.0 g of tetrabutylammonium bromide.

To this, 249.81 g (2.1 mols) of propargyl bromide were dropwise added at 80° C. for 5 hours under stirring and after completion of said addition, the combined was heated to 90° C. and reacted at the same temperature for 6 hours.

Thereafter, the dichloro ethane layer was separated, washed several times with deionized water and by using an evaporator, unreacted material and solvent were removed off to obtain a crude product, which was then purified by means of silica gel column chromatography.

Pure N,N,N',N'-tetra propargyl-p,p'-diamino diphenyl methane was obtained in 89% reaction field.

EXAMPLE 3

Into a reaction vessel fitted with a stirrer, a reflux condenser and a nitrogen gas inlet tube, were placed 100.19 g (0.5 mol) of 1,12-diamino dodecane, 63.15 g of sodium hydroxide, 180 g of deionized water, 180 g of methylene chloride and 1.0 g of tetrabutyl-ammonium bromide and to this, 190.34 g (1.6 mols) of propargyl bromide were dropwise added at 30° C. in 5 hours under stirring.

After completion of said addition, the mixture was heated to 60° C. and reacted at the same temperature for 6 hours.

Thereafter, methylene chloride layer was separated, washed several times with deionized water and by using an evaporator, unreacted material and solvent were removed off to obtain a crude product.

This was purified by silica gel column chromatography to obtain pure N,N,N'-tris propargyl-1,12-diamino dodecane in 85% yield.

EXAMPLE 4

Into a reaction vessel fitted with a stirrer, a reflux condenser and a nitrogen gas inlet tube, were placed 124.35 g (0.5 mol) of p,p'-diamino-diphenyl sulfone, 63.15 g of sodium hydroxide, 180 g of deionized water, 180 g of dichloroethane, and 1.0 g of tetrabutyl-ammonium bromide and to this, 190.34 g (1.6 mols) of propargyl bromide were dropwise added at 80° C. for 5 hours under stirring.

After completion of said addition, the combined was heated to 90° C. and reacted at the same temperature for 6 hours.

Thereafter, the dichloroethane layer was separated, washed several times with deionized water and by using an evaporater, unreacted meterial and solvent were removed off to obtain a crude product.

This was purified by using a silica gel column chromatography to obtain pure N,N,N'-tris-propargyl-p,p'-diamino diphenyl methane in 89% yield.

EXAMPLES 5-8

Using the amine derivatives shown in Table 1 as starting materials, the similar procedures were repeated as in the preceding Example and various propargyl compounds were prepared.

Properties of thus obtained products and reaction yields are shown in the Table 1.

TABLE 1

| | amine derivative | Pr—X | Product |
|---|---|---|---|
| 1 | $H_2N-CH_2-CH_2-NH_2$<br>0.5 mol (Mn: 60.1) | Pr—Br<br>2.1 mol | $(CH\equiv CH-CH_2)_2N-CH_2CH_2-N(CH_2-C\equiv CH)_2$ |
| 2 | $H_2N-\phi-CH_2-\phi-NH_2$<br>0.5 mol (Mn: 198.2) | Pr—Br<br>2.1 mol | $(CH\equiv C-CH_2)_2N-\phi-CH_2-\phi-N(CH_2-CH\equiv CH_2)_2$ |
| 3 | $H_2N-(CH_2)_{12}-NH_2$<br>0.5 mol (Mn: 200.4) | Pr—Br<br>1.6 mol | $(CH_2\equiv C-CH_2)_2N-(CH_2)_{12}-\overset{R}{\underset{|}{N}}-CH_2-C\equiv CH$<br>$R = -H, -CH_2-C\equiv CH$ |
| 4 | $H_2N-\phi-SO_2-\phi-NH_2$<br>0.5 mol (Mn: 248.7) | Pr—Br<br>1.6 mol | $(CH\equiv C-CH_2)_2N-\phi-SO_2-\phi-\overset{R}{\underset{|}{N}}-CH_2-C\equiv CH$<br>$R = -H, -CH_2-C\equiv CH$ |
| 5 | $HN[(CH_2)_3NH_2]_2$<br>0.5 mol (Mn: 131.2) | Pr—Br<br>2.7 mol | $CH\equiv C-CH_2-N(CH_2)_3N(CH_2-C\equiv CH)_2]_2$ |
| 6 | $CH_3-\phi-NH_2$<br>0.5 mol (Mn: 122.2) | Pr—Br<br>1.05 mol | $CH_3-\phi-N(CH_2-C\equiv CH)_2$ |
| 7 | $C_{10}H_6(NH_2)_2$<br>0.5 mol (Mn: 158.2) | Pr—Cl<br>2.2 mol | $C_{10}H_6[N(CH_2-C\equiv CH)_2]_2$<br>$\underset{R}{|}$<br>$R = -H, -CH_2-C\equiv CH$ |
| 8 | $H_2N-C_6F_4C_6F_4-NH_2$<br>0.5 mol (Mn: 328.2) | Pr—Cl<br>1.65 mol | $(CH\equiv C-CH_2)_2NC_6F_4C_6F_4N(CH_2-C\equiv CH)_2$ |

| | Y % | IR(cm$^{-1}$) | % of introduced $CH\equiv C-CH_2-$ group |
|---|---|---|---|
| 1 | 92 | $CH\equiv C-$ (3300 cm$^{-1}$, 2100 cm$^{-1}$)<br>$-CH_2-$ (2900 cm$^{-1}$) | 98 |
| 2 | 89 | $CH\equiv C-$ (3300 cm$^{-1}$, 2100 cm$^{-1}$)<br>$-\phi-$ (1610 cm$^{-1}$, 1510 cm$^{-1}$)<br>$\phi-N\diagdown$ (1340 cm$^{-1}$, 1210 cm$^{-1}$) | 100 |
| 3 | 73 | $CH\equiv C-$ (3300 cm$^{-1}$, 2100 cm$^{-1}$)<br>$-CH_2-$ (2900 cm$^{-1}$)<br>$CH_2-N$ (1210 cm$^{-1}$) | 52 |

TABLE 1-continued

| | | | | |
|---|---|---|---|---|
| 4 | 85 | CH≡C— | (3300 cm$^{-1}$, 2100 cm$^{-1}$) | 70 |
| | | —⟨O⟩— | (1600 cm$^{-1}$, 1500 cm$^{-1}$) | |
| | | —SO$_2$— | (1310 cm$^{-1}$, 1100 cm$^{-1}$) | |
| | | ⟨O⟩—N' | (1350 cm$^{-1}$, 1210 cm$^{-1}$) | |
| 5 | 50 | CH≡C— | (3300 cm$^{-1}$, 2100 cm$^{-1}$) | 100 |
| | | —CH$_2$— | (2900 cm$^{-1}$) | |
| 6 | 68 | CH≡C— | (3300 cm$^{-1}$, 2100 cm$^{-1}$) | 100 |
| | | —⟨O⟩— | (1600 cm$^{-1}$, 1500 cm$^{-1}$) | |
| | | ⟨O⟩—N' | (1350 cm$^{-1}$, 1210 cm$^{-1}$) | |
| 7 | 84 | CH≡C— | (3300 cm$^{-1}$, 2100 cm$^{-1}$) | 60 |
| | | ⟨OO⟩ | (1590 cm$^{-1}$, 1490 cm$^{-1}$) | |
| 8 | 85 | CH≡C— | (3300 cm$^{-1}$, 2100 cm$^{-1}$) | 100 |

Pr—X: Pr—Br (CH≡C—CH$_2$—Br: Mn = 118.96)
Pr—Cl (CH≡C—CH$_2$—Cl: Mn = 74.51)
% of introduced CH≡C—CH$_2$ group: $^1$H, $^{13}$C-NMR (Nippon Denshi-sha EX-90) Integral ratio of C<u>H</u>≡C—/-ph-<u>H</u>, integral ratio of CH≡C—/—C<u>H</u>$_2$— or —C<u>H</u>$_3$, integral ratio of <u>C</u>H≡C—/—C$_6$F$_4$— were first determined, from which the introduction % was calculated.

What is claimed is:

1. A propargyl compound represented by the formula:

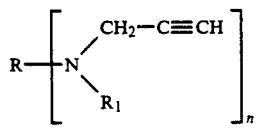

wherein R is an alkylene group having 1 to 20 carbon atom s; and alkylene group having 2 to 20 carbon atoms interrupted by —NH— group(s); or an aromatic group selected from the group consisting of diphenyl methane and diphenyl sulfone; said R being optionally substituted with a lower alkyl, halogen, nitro, lower alkoxy or cyano group; R$_1$ is a —CH$_2$—C≡CH group and n is an integer of 2 to 4.

2. A propargyl compound according to claim 1 in which R is an aromatic group selected from the group consisting of diphenyl methane and diphenyl sulfone.

3. A propargyl compound according to claim 2 in which R is diphenyl methane.

4. A propargyl compound according to claim 2 in which R is diphenyl sulfone.

5. A propargyl compound according to claim 1 in which n is 2.

6. A propargyl compound according to claim 1 in which n is 3.

7. A propargyl compound according to claim 1 in which n is 4.

* * * * *